United States Patent [19]
Hillman et al.

[11] Patent Number: 6,030,824
[45] Date of Patent: Feb. 29, 2000

[54] HUMAN N-ACETYLNEURAMINATE LYASE

[75] Inventors: Jennifer L. Hillman, Mountain View; Purvi Shah, Sunnyvale; Neil C. Corley, Mountain View, all of Calif.

[73] Assignee: Incyte Pharmaceuticals, Palo Alto, Calif.

[21] Appl. No.: 09/244,233

[22] Filed: Feb. 1, 1999

Related U.S. Application Data

[62] Division of application No. 09/027,013, Feb. 20, 1998.
[51] Int. Cl.[7] ...................................................... C12N 9/88
[52] U.S. Cl. ............................................................ 435/232
[58] Field of Search ............................................. 435/232

[56] References Cited

PUBLICATIONS

Hillier et al., Genbank Database, Accession No. W79930, Oct. 1998.
Lawrence, M. et al., J. Mol. Biol., vol.266, No. 2, pp. 381–399, Feb. 1997.
Vimr and Troy, Regulation of Sialic Acid Metabolism in *Escherichia coli*:Role of N–Acylneuraminate Pyruvate–Layase, *J. Bacteriol.*, 164:854–860 (1985).
Meysick, K.C. et al., Molecular characterization and expression of a N–acetylneuraminate lyase gene from *Trichomonas vaginalis, Mol. Biochem. Parasitol.*, 76:289–292 (1996) (GI 1016805, GI 10106806).
Misasi et al., Gangliosides and Autoimmune Diabetes, *Diabetes Metab. Rev.*, 13:163–179 (1997).
Ohta, Y. et al., GenBank Sequence Database (Accession X03345), National Center for Biotechnology Information: National Library of Medicine, Bethesda, Maryland 20849 (GI 42130, GI 42131).
Meysick, K.C. et al., GenBank Sequence Database (Accession U35878), National Center for Biotechnology Information: National Library of Medicine, Bethesda, Maryland 20849 (GI 1016805, GI 10106806).
Ohta, Y. et al., Complete nucleotide sequence of the *E. coli* N–acetylneuraminate lyase, *Nucleic Acid Res.*, 13:8843–8852 (1985) (GI 42130, GI 42131).

*Primary Examiner*—Ponnathapu Achutamurthy
*Assistant Examiner*—Peter P. Tung
*Attorney, Agent, or Firm*—Incyte Pharmaceuticals, Inc.

[57] ABSTRACT

The invention provides a human N-acetylneuraminate lyase (HNANL) and polynucleotides which identify and encode HNANL. The invention also provides expression vectors, host cells, antibodies, agonists, and antagonists. The invention also provides methods for treating or preventing disorders associated with expression of HNANL.

2 Claims, 8 Drawing Sheets

FIGURE 1A

```
5'  AAG AGC GGA   GGC CTG GAA   GGG GAA ACT   GAA GCA GAA   AGA GGT TAC   TTA ATG GGC
    10            19            28            37            46            55

TCA AGG TCA   CCT ACC TGA   CCT ACC AGC   AGC TCA ATG   GCC TTC CCA   AAG AAG AAA
    64            73            82            91            100           109
                                                M   A   F    P   K   K     K

CTT CAG GGT   CTT GTG GCT   GCA ACC ATC   ACG CCA ATG   ACT GAG AAT   GGA GAA ATC
    118           127           136           145           154           163
    L   Q   G     L   V   A     A   T   I     T   P   M     T   E   N     G   E   I

AAC TTT TCA   GTA ATT GGT   CAG TAT GTG   GAT TAT CTT   GTG AAA CAG   GGA GTG
    172           181           190           199           208           217
    N   F   S     V   I   G     Q   Y   V     D   Y   L     V   K   Q     G   V

AAG AAC ATT   TTT GTG AAT   GGC ACA GAA   GGC CTG TCC   CTG AGC GTC   TCA
    226           235           244           253           262           271
    K   N   I     F   V   N     G   T   E     G   L   S     L   S   V     S

GAG CGT CGC   CAG GTT GCA   GAG GAG TGG   GTG ACA AAA   GGG AAG GAC   AAG CTG GAT
    280           289           298           307           316           325
    E   R   R     Q   V   A     E   E   W     V   T   K     G   K   D     K   L   D

CAG GTG ATA   ATT CAC GTA   GGA GCA CTG   AGC TTG AAG   GAG TCA CAG   GAA CTG GCC
    334           343           352           361           370           379
    Q   V   I     I   H   V     G   A   L     S   L   K     E   S   Q     E   L   A
```

```
     388        397        406  415        424        433
CAA CAT GCA GCA GAA ATA GGA GCT GAT GGC ATC GTC ATT GCA CCG TTC TTC
 Q   H   A   A   E   I   G   A   D   G   I   A   V   I   A   P   F   F 442        451        460  469        478        487
CTC AAG CCA TGG ACC AAA GAT ATC CTG ATT AAT TTC CTA AAG GAA GTG GCT GCT
 L   K   P   W   T   K   D   I   L   I   N   F   L   K   E   V   A   A 496        505        514  523        532        541
GCC GCC CCT GCC CTG CCA TTT TAT TAC TAT CAC ATT CCT GCC TTG ACA GGG GTA
 A   A   P   A   L   P   F   Y   Y   Y   H   I   P   A   L   T   G   V 550        559        568  577        586        595
AAG ATT CGT GCT GAG GAG TTG GAT GGG ATT CTG GAT AAG ATC CCC ACC TTC
 K   I   R   A   E   E   L   D   G   I   L   D   K   I   P   T   F 604        613        622  631        640        649
CAA GGG CTG AAA TTC AGT GAT ACA GAT CTC TTA GAC TTC GGG CAA TGT GTT GAT
 Q   G   L   K   F   S   D   T   D   L   L   D   F   G   Q   C   V   D 658        667        676  685        694        703
CAG AAT CGC CAG CAA CAG TTT GCT TTC CTT TTT GGG GTG GAT GAG CAA TTG TTG
 Q   N   R   Q   Q   Q   F   A   F   L   F   G   V   D   E   Q   L   L 712        721        730  739        748        757
AGT GCT CTG GTG ATG GGA GCA ACT GGA GCA GTG GGC AGT ACC TAT AAC TAC CTG
 S   A   L   V   M   G   A   T   G   A   V   G   S   T   Y   N   Y   L
```

FIGURE 1B

```
       766          775          784          793          802          811
GGA AAA AAG ACA AAC CAG ATG TTG GAG GCT TTT GAA CAA AAG GAC TTC TCT TTA
 G   K   K   T   N   Q   M   L   E   A   F   E   Q   K   D   F   S   L 820          829          838          847          856          865
GCC CTG AAC TAT CAG TTT TGT ATC CAG AGA TTT ATC AAC TTT GTT GTC AAA CTA
 A   L   N   Y   Q   F   C   I   Q   R   F   I   N   F   V   V   K   L 874          883          892          901          910          919
GGT TTT GGA GTG TCA CAG ACC AAA GCC ATC ATG ACT CTG GTC TCT GGG ATT CCA
 G   F   G   V   S   Q   T   K   A   I   M   T   L   V   S   G   I   P 928          937          946          955          964          973
ATG GGC CCA CCC CGG CTT CCA CAG AAA TCC AGG GAG TTT ACT GAT AGT
 M   G   P   P   R   L   P   Q   K   A   S   R   E   F   T   D   S 982          991         1000         1009         1018         1027
GCT GAA GCT AAA CTG AAG AGC CTG GAT TTC CTT TCT TTC ACT GAT TTA AAG GAT
 A   E   A   K   L   K   S   L   D   F   L   S   F   T   D   L   K   D 1036         1045         1054         1063         1072         1081
GGA AAC TTG GAA GCT GGT AGC TAG TGC CTC TCT ATC AAA TCA GGG TTT GCA CCT
 G   N   L   E   A   G   S 1090         1099         1108         1117         1126         1135
GCT GAA ATA ATC TAC CTT AAA TAG TGC ATT TTT TTC TCA GGG AAT TTT AGA TGA 1144         1153         1162         1171         1180         1189
ACT TGA ATA AAC TCT CCT AGC AAA TGA AAT CTC ACA ATA AGC ATT GAG GTA CCT
```

FIGURE 1C

```
              1198           1207           1216           1225           1234           1243
TTT GTG AGC CTT AAA AAG TCT TAT TTT GTG AAG GGG CAA AAA CTC TAG GAG TCA 1252           1261           1270           1279           1288           1297
CAA CTC TCA GTC ATT CAT TTC ACA GAT TTT GTG GAG AAA TTT CTG TTT ATA 1306           1315           1324           1333           1342           1351
TGG ATG AAA TGG AAT CAA GAG GAA AAT TGT AAT TGA TTA ATT CCA TCT GTC TTT 1360           1369           1378           1387           1396           1405
AGG AGC TCT CAT TAT CTC GGT CTC TGG TTC CTA ATC CTA TTT TAA AGT TGT CTA 1414           1423           1432           1441           1450           1459
ATT TTA AAC CAC TAT AAT ATG TCT TCA TTT TAA TAA ATA TTC ATT TGG AAT CTA 1468           1477           1486           1495           1504           1513
GGA AAA CTC TGA GCT ACT GCA TTT AGG CAG GCA CTT TAA TAC CAA ACT GTA ACA 1522           1531           1540           1549           1558           1567
TGT CTC AAC TGT ATA CAA CTC AAA ATA CAC CAG CTC ATT TGG CTG CTC AGT CTA 1576           1585           1594           1603           1612           1621
ACT CTA GAA TGG ATG CTT TTG AAT TCA TTT CGA TGT CAC CAC TTT TCG CTC TTT 1630           1639           1648           1657           1666           1675
AAA AAC ACT GGG TCA GGT GAG GAC TTG TTT CAG TTC CTA TAA CTA AGT AAA GGG 1684           1693           1702           1711           1720           1729
CGG CTT TCT CAT AAC AAA GGA AAA AGT CTT CCC CAA AGA TGA ATT TAA GTC TCC
```

FIGURE 1D

```
                              1738        1747        1756        1765        1774        1783
                        ACT TTT TTC TAT ACA GAA AAC TCA AAA CTC AAA GTT TCA AAG AAC CAA AGG ACT 1792        1801        1810        1819        1828        1837
        CTT CCT CTG GGC ACC ACA AAC TTC CCC TTC CTC CAC TGA GAA GAC TGT CTC TCC 1846        1855        1864        1873        1882        1891
        CGC AGG ACC CTG AAT TAT TGA AAT CGA AGG CTG ACT TCC TTT CTG CAG TGA GCC 1900        1909        1918        1927        1936        1945
        CAG GGG CTA ATG TTA TTA TCC TGT CAC ACT TGC AAC TAG TGA CTT TTG TTT AGT 1954        1963        1972        1981        1990        1999
        GAT AGA AGA TTT GGG GAG GAC CCA AAG GAC TCA GAA CTT TCT CTC CAT ACC TCC 2008        2017        2026        2035        2044        2053
        TTT TAC TCT TTT CTT TCT GTG TAA TGT ATC AAC AAC TGT TTA ATC TCC CTT CTA 2062        2071        2080        2089        2098        2107
        ACA AAC CTT GAT ATA AGC TTT CTG ATA TCA AAG TAT ATT GAC AGT TAA CCC TTA 2116        2125        2134        2143        2152        2161
        CTG ATT TTA AAC TTG ACT ATC CAG TCT GTT AAT TAC CTA AGA TTT TGT TTT CAT 2170        2179        2188        2197        2206        2215
        TTC ATC TCT AAT TGT TTT GAT CAT TGG CAG AGA AAG AGT ATT TGA AAT TCA TAT 2224        2233        2242        2251        2260        2269
        CAG TTT TGC TCC TTA TTT TAA TCT CTT TGA ATT AAA AAT AAA ACT TTT TCA AAA
```

FIGURE 1E

```
         2278           2287           2296          2305           2314           2323
TGG AAA TTT GAA ATT ATA AGT AGA CTT CAA TTA TCT TTG CTA ATC CTC TCT TTA
         2332           2341           2350          2359           2368           2377
ATT AGT CAG CTA GTT AAA AGT TGT TAT ATT CAT ATA TCC TCA ACC CTC TTT TTG
         2386           2395           2404          2413           2422           2431
CCT TTG TAG CTT TTA ATT TCC TGA AAG AAA ATG AGT TGT TCG TTT TTG GTT
         2440           2449           2458          2467           2476           2485
CTG AGG ATG TGA TAT CCG TAC TTA CTG ATA CTA AAG CCA AAT TTA AAT TCT AAA
         2494           2503           2512          2521           2530
ATT AAT TCT TGG GTA TCC AAT AAA CAA AGA ACT ATT TTT CAA AAA AAA AAA  3'
```

| | | | | | |
|---|---|---|---|---|---|
| 160 | DGILDKIPTFQGLKFSDTDLLDFGQCVDQN | 2125668 |
| 153 | -NTLVTLPGVGALKQTSGDLYQMEQ-IRRE | GI 42131 |
| 177 | -GELFENPKIIGVKFTAGDFYLLER-VKRA | GI 1016806 |
| | | |
| 190 | RQQFAFLFGVDEQLLSALVMGATGAVGST | 2125668 |
| 181 | HPDLVLYN-GYDEIFASGLLAGADGGIGST | GI 42131 |
| 205 | YPDHLIWA-GFDEMMLPACSLGIDGAIGST | GI 1016806 |
| | | |
| 220 | YNYLGKKTNQMLEAFEQKDFSLALNYQFCI | 2125668 |
| 210 | YNIMGWRYQGIVKALKEGDIQTAQKLQTEC | GI 42131 |
| 234 | FNVNAKRARQIFELSKAGKYDEALEVQHVT | GI 1016806 |
| | | |
| 250 | QRFINFVVKLGFGVSQTKAIMTLVSGIPMG | 2125668 |
| 240 | NKVIDLLIKTGV-FRGLKTVLHYMDVVSVP | GI 42131 |
| 264 | NDLIAGILSNGL-YLTIKELMR-LDGVDAG | GI 1016806 |
| | | |
| 280 | PPRLPLQKASREFTDSAEAKLKSLDFLSFT | 2125668 |
| 269 | LCRKP---FGPVDEKYQPELK-------- | GI 42131 |
| 292 | YCREPMTKALTPAQVAFAKQLK-------- | GI 1016806 |
| | | |
| 310 | DLKDGNLEAGS | 2125668 |
| 287 | ALAQQLMQERG | GI 42131 |
| 314 | E--KYLL | GI 1016806 |

HUMAN N-ACETYLNEURAMINATE LYASE

This application is a divisional application of U.S. application Ser. No. 09/027,013, filed on Feb. 20, 1998.

FIELD OF THE INVENTION

This invention relates to nucleic acid and amino acid sequences of a human N-acetylneuraminate lyase and to the use of these sequences in the diagnosis, treatment, and prevention of cancer and autoimmune disorders.

BACKGROUND OF THE INVENTION

N-acetylneuraminate lyase (NANL), also known as N-acetylneuraminate aldolase, and acylneuraminate-pyruvate lyase, is an enzyme that catalyzes the conversion of N-acetylneuraminic acid (sialic acid) into pyruvate and N-acetyl-D-mannosamine, as well as the reverse reaction. In bacteria, NANL is involved in energy metabolism, and the degradation of sialic acid produces usable carbon and energy sources for the bacteria. The expression and activity of NANL in bacteria are regulated by the level of sialic acid. (Vimr, E. R. and Troy, F. A. (1985) J. Bacteriol. 164:854–860.) NANL has been described in a number of mammalian tissues where it is a key enzyme in sialic acid metabolism.

Sialic acid is an essential constituent of a class of glycolipids known as gangliosides. Gangliosides are composed of a lipid component, ceramide, and an oligosaccharide component. The oligosaccharide component always includes sialic acid and may contain other sugars such as glucose, galactose, and N-acetylgalactosamine. Gangliosides were first described in neural tissue, particularly in grey matter, but have since been shown to exist in nearly all tissues. Gangliosides are components of the cell membrane, and they act as receptors for a variety of molecules and participate in cell-to-cell interactions and in signal transduction. Gangliosides are also found in the membranes of intracellular organelles, such as secretory granules, where their roles are less well-defined. Defects in ganglioside expression are important in some disease processes including two forms of storage defects, $GM_2$ gangliosidosis, Tay-Sachs/$\beta$-hexosaminidase deficiency, and $GM_1$ gangliosidosis, $\beta$-galactosidase deficiency. The accumulation of gangliosides in the lysosomes of neurons is characteristic of these diseases. In addition auto-antibodies to gangliosides have been demonstrated in a number of autoimmune disorders including multiple sclerosis, lupus erythematosus, and type I diabetes mellitus. Thus, aberrations in sialic acid metabolism and NANL are involved in autoimmune disorders. (Meysick, K. C. et al. (1996) Mol. Biochem. Parasitol. 76:289–292; Misasi, R. et al. (1997) Diabetes Metab. Rev. 13:163–179).

The discovery of a new human N-acetylneuraminate lyase and the polynucleotides encoding it satisfies a need in the art by providing new compositions which are useful in the diagnosis, treatment, and prevention of cancer and autoimmune disorders.

SUMMARY OF THE INVENTION

The invention is based on the discovery of a new human N-acetylneuraminate lyase (HNANL), the polynucleotides encoding HNANL, and the use of these compositions for the diagnosis, treatment, or prevention of cancer and autoimmune disorders.

The invention features a substantially purified polypeptide comprising the amino acid sequence of SEQ ID NO: 1 or a fragment of SEQ ID NO:1.

The invention further provides a substantially purified variant having at least 90% amino acid sequence identity to the amino acid sequence of SEQ ID NO:1 or a fragment of SEQ ID NO:1. The invention also provides an isolated and purified polynucleotide encoding the polypeptide comprising the sequence of SEQ ID NO:1 or a fragment of SEQ ID NO:1. The invention also includes an isolated and purified polynucleotide variant having at least 90% polynucleotide sequence identity to the polynucleotide encoding the polypeptide comprising the amino acid sequence of SEQ ID NO:1 or a fragment of SEQ ID NO:1.

The invention further provides an isolated and purified polynucleotide which hybridizes under stringent conditions to the polynucleotide encoding the polypeptide comprising the amino acid sequence of SEQ ID NO:1 or a fragment of SEQ ID NO:1, as well as an isolated and purified polynucleotide which is complementary to the polynucleotide encoding the polypeptide comprising the amino acid sequence of SEQ ID NO:1 or a fragment of SEQ ID NO:1.

The invention also provides an isolated and purified polynucleotide comprising the polynucleotide sequence of SEQ ID NO:2 or a fragment of SEQ ID NO:2, and an isolated and purified polynucleotide variant having at least 90% polynucleotide sequence identity to the polynucleotide comprising the polynucleotide sequence of SEQ ID NO:2 or a fragment of SEQ ID NO:2. The invention also provides an isolated and purified polynucleotide having a sequence complementary to the polynucleotide comprising the polynucleotide sequence of SEQ ID NO:2 or a fragment of SEQ ID NO:2.

The invention further provides an expression vector containing at least a fragment of the polynucleotide encoding the polypeptide comprising the sequence of SEQ ID NO:1 or a fragment of SEQ ID NO:1. In another aspect, the expression vector is contained within a host cell.

The invention also provides a method for producing a polypeptide comprising the amino acid sequence of SEQ ID NO:1 or a fragment of SEQ ID NO:1, the method comprising the steps of: (a) culturing the host cell containing an expression vector containing at least a fragment of a polynucleotide encoding the polypeptide comprising the amino acid sequence of SEQ ID NO:1 or a fragment of SEQ ID NO:1 under conditions suitable for the expression of the polypeptide; and (b) recovering the polypeptide from the host cell culture.

The invention also provides a pharmaceutical composition comprising a substantially purified polypeptide having the sequence of SEQ ID NO:1 or a fragment of SEQ ID NO:1 in conjunction with a suitable pharmaceutical carrier.

The invention further includes a purified antibody which binds to a polypeptide comprising the sequence of SEQ ID NO:1 or a fragment of SEQ ID NO:1, as well as a purified agonist and a purified antagonist of the polypeptide.

The invention also provides a method for treating or preventing a cancer, the method comprising administering to a subject in need of such treatment an effective amount of an antagonist of HNANL.

The invention also provides a method for treating or preventing an autoimmune disorder, the method comprising administering to a subject in need of such treatment an effective amount of an antagonist of HNANL.

The invention also provides a method for detecting a polynucleotide encoding a polypeptide comprising the amino acid sequence of SEQ ID NO:1 or a fragment of SEQ ID NO:1 in a biological sample containing nucleic acids, the method comprising the steps of: (a) hybridizing the complement of the polynucleotide encoding the polypeptide comprising the amino acid sequence of SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding the polypeptide comprising the amino acid sequence of SEQ ID NO:1 or a fragment of SEQ ID NO:1 in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, 1E, and 1F show the amino acid sequence (SEQ ID NO:1) and nucleic acid sequence (SEQ ID NO:2) of HNANL. The alignment was produced using MACDNASIS PRO™ software (Hitachi Software Engineering Co. Ltd., San Bruno, Calif.).

FIGS. 2A and 2B show the amino acid sequence alignments among HNANL (Incyte Clone number; SEQ ID NO:1), N-acetylneuraminate lyase from *Escherichia coli* (GI 42131; SEQ ID NO:3), and N-acetylneuraminate lyase from *Trichomonas vaginalis* (GI 1016806; SEQ ID NO:4), produced using the multisequence alignment program of LASERGENE software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

DEFINITIONS

"HNANL," as used herein, refers to the amino acid sequences of substantially purified HNANL obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to HNANL, increases or prolongs the duration of the effect of HNANL. Agonists may include proteins, nucleic acids, carbohydrates, or any other molecules which bind to and modulate the effect of HNANL.

An "allele" or an "allelic sequence," as these terms are used herein, is an alternative form of the gene encoding HNANL. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HNANL, as described herein, include those sequences with deletions, insertions, or substitutions of different nucleotides, resulting in a polynucleotide the same as HNANL or a polypeptide with at least one functional characteristic of HNANL. Included within this definition are polymorphisms which may or may not be readily detectable using a particular oligonucleotide probe of the polynucleotide encoding HNANL, and improper or unexpected hybridization to alleles, with a locus other than the normal chromosomal locus for the polynucleotide sequence encoding HNANL. The encoded protein may also be "altered," and may contain deletions, insertions, or substitutions of amino acid residues which produce a silent change and result in a functionally equivalent HNANL. Deliberate amino acid substitutions may be made on the basis of similarity in polarity, charge, solubility, hydrophobicity, hydrophilicity, and/or the amphipathic nature of the residues, as long as the biological or immunological activity of HNANL is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of HNANL which are preferably about 5 to about 15 amino acids in length and which retain some biological activity or immunological activity of HNANL. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual,* Cold Spring Harbor Press, Plainview, N.Y., pp. 1–5.)

The term "antagonist," as it is used herein, refers to a molecule which, when bound to HNANL, decreases the amount or the duration of the effect of the biological or immunological activity of HNANL. Antagonists may include proteins, nucleic acids, carbohydrates, antibodies, or any other molecules which decrease the effect of HNANL.

As used herein, the term "antibody" refers to intact molecules as well as to fragments thereof, such as Fa, F(ab')$_2$, and Fv fragments, which are capable of binding the epitopic determinant. Antibodies that bind HNANL polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic HNANL, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding HNANL or fragments of HNANL may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

The phrase "consensus sequence," as used herein, refers to a nucleic acid sequence which has been resequenced to resolve uncalled bases, extended using XL-PCR kit (Perkin Elmer, Norwalk, Conn.) in the 5' and/or the 3' direction, and resequenced, or which has been assembled from the overlapping sequences of more than one Incyte Clone using a computer program for fragment assembly, such as the GEL-VIEW Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding HNANL, by northern analysis is indicative of the presence of nucleic acids encoding HNANL in a sample, and thereby correlates with expression of the transcript from the polynucleotide encoding HNANL.

A "deletion," as the term is used herein, refers to a change in the amino acid or nucleotide sequence that results in the absence of one or more amino acid residues or nucleotides.

The term "derivative," as used herein, refers to the chemical modification of HNANL, of a polynucleotide sequence encoding HNANL, or of a polynucleotide sequence complementary to a polynucleotide sequence encoding HNANL. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign program (software, DNASTAR, Inc., Madison Wis.). The MegAlign program can create alignments between two or more sequences according to different methods, e.g., the Clustal Method (Higgins, D. G. and P. M. Sharp (1988) Gene 73:237–244). The Clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be calculated by the Clustal Method, or by other methods known in the art, such as the Jotun Hein Method. (See, e.g., Hein, J. (1990) Methods in Enzymology 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an array of distinct polynucleotides or oligonucleotides arrayed on a substrate, such as paper, nylon or any other type of membrane, filter, chip, glass slide, or any other suitable solid support.

The term "modulate," as it appears herein, refers to a change in the activity of HNANL. For example, modulation may cause an increase or a decrease in protein activity, binding characteristics, or any other biological, functional, or immunological properties of HNANL.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The terms "operably associated" or "operably linked," as used herein, refer to functionally related nucleic acid sequences. A promoter is operably associated or operably linked with a coding sequence if the promoter controls the transcription of the encoded polypeptide. While operably associated or operably linked nucleic acid sequences can be contiguous and in reading frame, certain genetic elements, e.g., repressor genes, are not contiguously linked to the encoded polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimers," "primers," "oligomers," and "probes," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding HNANL, or fragments thereof, or HNANL itself may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences.

Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5× SSPE, 0.3% SDS, and 200 μg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, and refers to cells which transiently express the inserted DNA or RNA for limited periods of time.

A "variant" of HNANL, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE (DNASTAR) software.

THE INVENTION

The invention is based on the discovery of a new human N-acetylneuraminate lyase (HNANL), the polynucleotides encoding HNANL, and the use of these compositions for the diagnosis, treatment, or prevention of cancer and autoimmune disorders.

Nucleic acids encoding the HNANL of the present invention were first identified in Incyte Clone 2125668 from the breast tissue cDNA library (BRSTNOT07) using a computer search for amino acid sequence alignments. A consensus sequence, SEQ ID NO:2, was derived from the following overlapping and/or extended nucleic acid sequences: Incyte Clones 2125668 (BRSTNOT07), 3342723 (SPLNNOT09), 517880 (MMLR1DT01), 632730 (NEUTGMT01), 1489108 (BRSTNOT08), 1927066 (BRSTNOT02), 1528550 (UCMCL5T01), and 2118915 (BRSTTUT02).

Figure 2A:
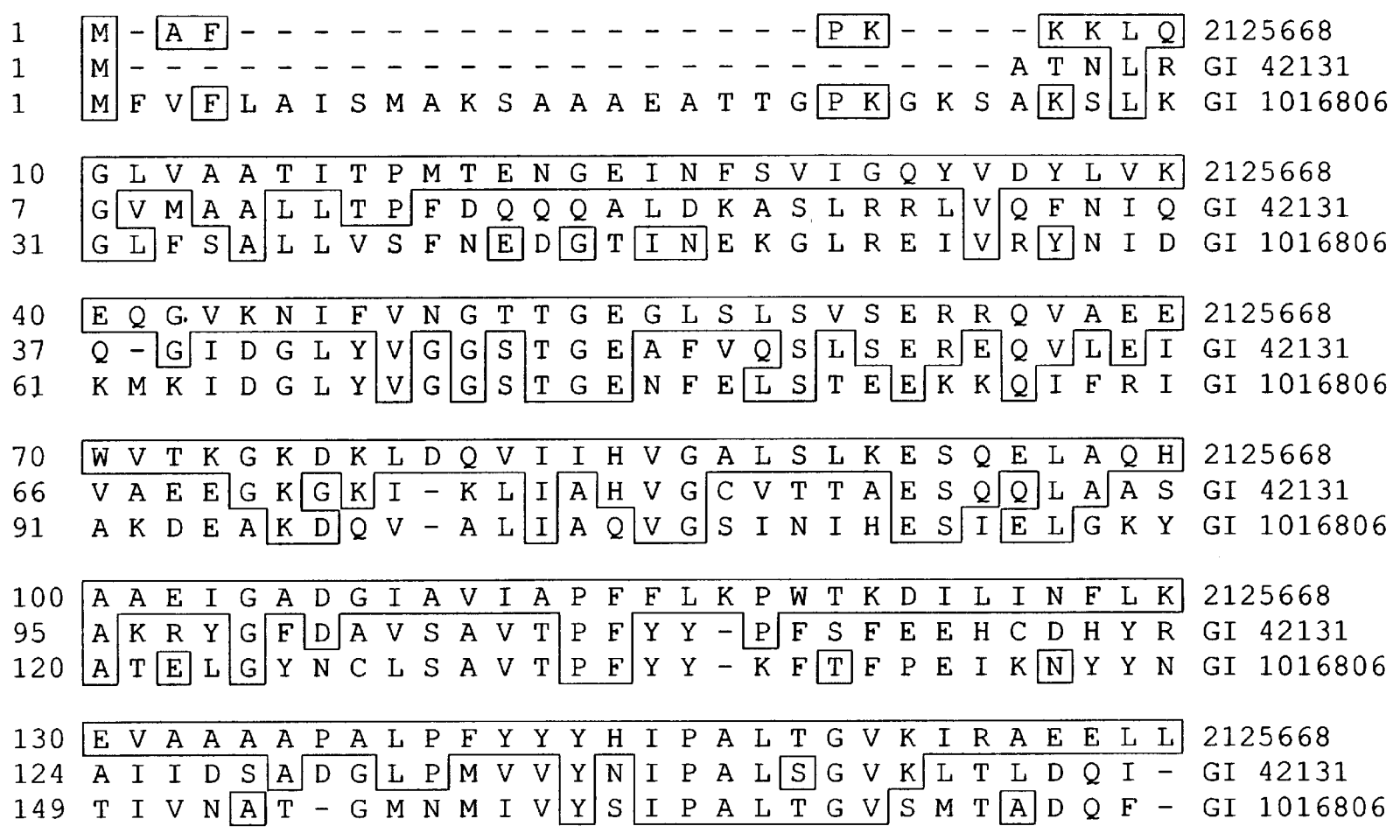

In one embodiment, the invention encompasses a polypeptide comprising the amino acid sequence of SEQ ID NO:1, as shown in FIGS. 1A, 1B, 1C, 1D 1E, and 1F. HNANL is 320 amino acids in length and has a potential dihydrodipicolinate synthetase signature sequence from $N_{45}$ through $E_{62}$. In addition, HNANL has a potential amidation site at $L_{223}$, two potential N-glycosylation sites at $N_{26}$ and $N_{49}$, five potential casein kinase II phosphorylation sites at $T_{51}$, $S_{59}$, $S_{89}$, $S_{175}$, and $S_{307}$, and two potential protein kinase C phosphorylation sites at $S_{61}$ and $S_{89}$. As shown in FIGS. 2A and 2B, HNANL has chemical and structural homology with N-acetylneuraminate lyase from *Escherichia coli* (ENANL) (GI 4213 1; SEQ ID NO:3), and from *Trichomonas vaginalis* (TNANL) (GI 1016806; SEQ ID NO:4). In particular, HNANL and ENANL share 23% identity, while HNANL and TNANL share 22% identity. In addition, HNANL shares 94% similarity with both ENANL and TNANL in the dihydrodipicolinate synthetase signature sequence region, which also contains three conserved phosphorylation sites. Outside this region, HNANL and ENANL share two phosphorylation sites, while HNANL and TNANL share one phosphorylation site. The fragment of SEQ ID NO:2 from about nucleotide 90 to about nucleotide 150 is useful as a hybridization probe. Northern analysis shows the expression of this sequence in various libraries, at least 43% of which are immortalized or cancerous and at least 37% of which involve the immune response. Of particular note is the expression of HNANL in libraries from cardiovascular tissue and hematopoietic or immune tissues.

The invention also encompasses HNANL variants. A preferred HNANL variant is one which has at least about 80%, more preferably at least about 90%, and most preferably at least about 95% amino acid sequence identity to the HNANL amino acid sequence, and which contains at least one functional or structural characteristic of HNANL.

The invention also encompasses polynucleotides which encode HNANL. In a particular embodiment, the invention encompasses a polynucleotide sequence comprising the sequence of SEQ ID NO:2, which encodes an HNANL.

The invention also encompasses a variant of a polynucleotide sequence encoding HNANL. In particular, such a variant polynucleotide sequence will have at least about 80%, more preferably at least about 90%, and most preferably at least about 95% polynucleotide sequence identity to the polynucleotide sequence encoding HNANL. A particular aspect of the invention encompasses a variant of SEQ ID NO:2 which has at least about 80%, more preferably at least about 90%, and most preferably at least about 95% polynucleotide sequence identity to SEQ ID NO:2. Any one of the polynucleotide variants described above can encode an amino acid sequence which contains at least one functional or structural characteristic of HNANL.

It will be appreciated by those skilled in the art that as a result of the degeneracy of the genetic code, a multitude of polynucleotide sequences encoding HNANL, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HNANL, and all such variations are to be considered as being specifically disclosed.

Although nucleotide sequences which encode HNANL and its variants are preferably capable of hybridizing to the nucleotide sequence of the naturally occurring HNANL under appropriately selected conditions of stringency, it may be advantageous to produce nucleotide sequences encoding HNANL or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HNANL and its derivatives without altering the encoded amino acid sequences include the production of RNA transcripts having more desirable properties, such as a greater half-life, than transcripts produced from the naturally occurring sequence.

The invention also encompasses production of DNA sequences which encode HNANL and HNANL derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HNANL or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, under various conditions of stringency. (See, e.g., Wahl, G. M. and S. L. Berger (1987) Methods Enzymol. 152:399–407; and Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, SEQUENASE (US Biochemical Corp., Cleveland, Ohio), Taq polymerase (Perkin Elmer), thermostable T7 polymerase (Amersham Pharmacia, Biotech, Piscataway, N.J.), or combinations of polymerases and proofreading exonucleases such as those found in the ELONGASE Amplification System (Life Technologies, Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding HNANL may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (See, e.g., Sarkar, G. (1993) PCR Methods Applic. 2:318–322.) In particular, genomic DNA is first amplified in the presence of a primer complementary to a linker sequence within the vector and a primer specific to the region predicted to encode the gene. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (See, e.g., Triglia, T. et al. (1988) Nucleic Acids Res. 16:8186.) The primers may be designed using commercially available software such as OLIGO 4.06 Primer Analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (See, e.g., Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Other methods which may be used to retrieve unknown sequences are known in the art. (See, e.g., Parker, J. D. et al. (1991) Nucleic Acids Res. 19:3055–3060.) Additionally, one may use PCR, nested primers, and PROMOTERFINDER libraries (Clontech, Palo Alto, Calif.) to walk genomic DNA. This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., GENOTYPER and SEQUENCE NAVIGATOR, Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HNANL may be used in recombinant DNA molecules to direct expression of HNANL, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HNANL.

As will be understood by those of skill in the art, it may be advantageous to produce HNANL-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HNANL-encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HNANL may be ligated to a heterologous sequence to encode a fusion protein. For example, to screen peptide libraries for inhibitors of HNANL activity, it may be useful to encode a chimeric HNANL protein that can be recognized by a commercially available antibody. A fusion protein may also be engineered to contain a cleavage site located between the HNANL encoding sequence and the heterologous protein sequence, so that HNANL may be cleaved and purified away from the heterologous moiety.

In another embodiment, sequences encoding HNANL may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, the protein itself may be produced using chemical methods to synthesize the amino acid sequence of HNANL, or a fragment thereof. For example, peptide synthesis can be performed using various solid-phase techniques. (See, e.g., Roberge, J. Y. et al. (1995) Science 269:202–204.) Automated synthesis may be achieved using the ABI 431A Peptide Synthesizer (Perkin Elmer).

The newly synthesized peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1983) *Proteins, Structures and Molecular Properties,* WH Freeman and Co., New York, N.Y.) Additionally, the amino acid sequence of HNANL, or any part thereof, may be altered during direct synthesis and/or combined with sequences from other proteins, or any part thereof, to produce a variant polypeptide.

In order to express a biologically active HNANL, the nucleotide sequences encoding HNANL or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding HNANL and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual,* Cold Spring Harbor Press, Plainview, N.Y., ch. 4, 8, and 16–17; and Ausubel, F. M. et al. (1995, and periodic supplements) *Current Protocols in Molecular Biology,* John Wiley & Sons, New York, N.Y., ch. 9, 13, and 16.)

A variety of expression vector/host systems may be utilized to contain and express sequences encoding HNANL. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions, e.g., enhancers, promoters, and 5' and 3' untranslated regions, of the vector and polynucleotide sequences encoding HNANL which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters, e.g., hybrid lacZ promoter of the BLUESCRIPT phagemid (Stratagene, La Jolla, Calif.) or PSPORT1 plasmid Life Technologies, may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HNANL, vectors based on SV40 or EBV may be used with an appropriate selectable marker.

In bacterial systems, a number of expression vectors may be selected depending upon the use intended for HNANL. For example, when large quantities of HNANL are needed for the induction of antibodies, vectors which direct high level expression of fusion proteins that are readily purified may be used. Such vectors include, but are not limited to, multifunctional *E. coli* cloning and expression vectors such as BLUESCRIPT (Stratagene), in which the sequence encoding HNANL may be ligated into the vector in frame with sequences for the amino-terminal Met and the subsequent 7 residues of β-galactosidase so that a hybrid protein is produced, and pIN vectors. (See, e.g., Van Heeke, G. and S. M. Schuster (1989) J. Biol. Chem. 264:5503–5509.) pGEX vectors (Amersham Pharmacia Biotech) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae,* a number of vectors containing constitutive or inducible promoters, such as alpha factor, alcohol oxidase, and PGH, may be used. (See, e.g., Ausubel, supra; and Grant et al. (1987) Methods Enzymol. 153:516–544.)

In cases where plant expression vectors are used, the expression of sequences encoding HNANL may be driven by any of a number of promoters. For example, viral promoters such as the 35S and 19S promoters of CaMV may be used alone or in combination with the omega leader sequence from TMV (Takamatsu, N. (1987) EMBO J. 6:307–311) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, e.g., Hobbs, S. or Murry, L. E. in *McGraw Hill Yearbook of Science and Technology* (1992) McGraw Hill, New York, N.Y.; pp. 191–196.)

An insect system may also be used to express HNANL. For example, in one such system, *Autographa californica* nuclear polyhedrosis virus (AcNPV) is used as a vector to express foreign genes in *Spodoptera frugiperda* cells or in Trichoplusia larvae. The sequences encoding HNANL may be cloned into a non-essential region of the virus, such as the polyhedrin gene, and placed under control of the polyhedrin promoter. Successful insertion of sequences encoding HNANL will render the polyhedrin gene inactive and produce recombinant virus lacking coat protein. The recombinant viruses may then be used to infect, for example, *S. frugiperda* cells or Trichoplusia larvae in which HNANL may be expressed. (See, e.g., Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding HNANL may be ligated into an adenovirus transcription/translation complex consisting of the late promoter and tripartite leader sequence. Insertion in a non-essential E1 or E3 region of the viral genome may be used to obtain a viable virus which is capable of expressing HNANL in infected host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding HNANL. Such signals include the ATG initiation codon and adjacent sequences. In cases where sequences encoding HNANL and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used. (See, e.g., Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing HNANL can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes and adenine phosphoribosyltransferase genes, which can be employed in $tk^-$ or $apr^-$ cells, respectively. (See, e.g., Wigler, M. et al. (1977) Cell 11:223–232; and Lowy, I. et al. (1980) Cell 22:817–823) Also, antimetabolite, antibiotic, or herbicide resistance can be used as the basis for selection. For example, dhfr confers resistance to methotrexate; npt confers resistance to the aminoglycosides, neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB, which allows cells to utilize indole in place of tryptophan, or hisD, which allows cells to utilize histinol in place of histidine. (See, e.g., Hartman, S. C. and R. C. Mulligan (1988) Proc. Natl. Acad. Sci. 85:8047–8051.) Recently, the use of visible markers has gained popularity with such markers as anthocyanins, B glucuronidase and its substrate GUS, luciferase and its substrate luciferin. Green fluorescent proteins (GFP; Clontech) are also used (See, e.g., Chalfie, M. et al. (1994) Science 263:802–805.) These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding HNANL is inserted within a marker gene sequence, transformed cells containing sequences encoding HNANL can be identified by the absence of marker gene function. Alternatively, a marker gene can be placed in tandem with a sequence encoding HNANL under the control of a single promoter. Expression of the marker gene in response to induction or selection usually indicates expression of the tandem gene as well.

Alternatively, host cells which contain the nucleic acid sequence encoding HNANL and express HNANL may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding HNANL can be detected by DNA-DNA or DNA-RNA hybridization or amplification using probes or fragments or fragments of polynucleotides encoding HNANL. Nucleic acid amplification based assays involve the use of oligonucleotides or oligomers based on the sequences encoding HNANL to detect transformants containing DNA or RNA encoding HNANL.

A variety of protocols for detecting and measuring the expression of HNANL, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HNANL is preferred, but a competitive binding assay may be employed. These and other assays are well described in the art. (See, e.g., Hampton, R. et al. (1990) *Serological Methods, a Laboratory Manual*, APS Press, St Paul, Minn., Section IV; and Maddox, D. E. et al. (1983) J. Exp. Med. 158:1211–1216.)

A wide variety of labels and conjugation techniques are known by those skilled in the art and may be used in various nucleic acid and amino acid assays. Means for producing labeled hybridization or PCR probes for detecting sequences related to polynucleotides encoding HNANL include oligolabeling, nick translation, end-labeling, or PCR amplification using a labeled nucleotide. Alternatively, the sequences encoding HNANL, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HNANL may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HNANL may be designed to contain signal sequences which direct secretion of HNANL through a prokaryotic or eukaryotic cell membrane. Other constructions may be used to join sequences encoding HNANL to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif.), between the purification domain and the HNANL encoding sequence may be used to facilitate purification. One such expression vector provides for expression of a fusion protein containing HNANL and a nucleic acid encoding 6 histidine residues preceding a thioredoxin or an enterokinase cleavage site. The histidine residues facilitate purification on immobilized metal ion affinity chromatography. (IMAC; see, e.g., Porath, J. et al. (1992) Prot. Exp. Purif. 3: 263–281.) The enterokinase cleavage site provides a means for purifying HNANL from the fusion protein. (See, e.g., Kroll, D. J. et al. (1993) DNA Cell Biol. 12:441–453.)

Fragments of HNANL may be produced not only by recombinant production, but also by direct peptide synthesis using solid-phase techniques. (See, e.g., Creighton, T. E. (1984) Protein: Structures and Molecular Properties, pp. 55–60, W.H. Freeman and Co., New York, N.Y.) Protein synthesis may be performed by manual techniques or by automation. Automated synthesis may be achieved, for example, using the Applied Biosystems 431A Peptide Synthesizer (Perkin Elmer). Various fragments of HNANL may be synthesized separately and then combined to produce the full length molecule.

THERAPEUTICS

Chemical and structural homology exists among HNANL and N-acetylneuraminate lyase from *Escherichia coli* (ENANL) (GI 42131), and from *Trichomonas vaginalis* (TNANL) (GI 1016806). In addition, HNANL is expressed in libraries from cancerous and immune tissues. Therefore, HNANL appears to play a role in cancer and autoimmune disorders.

Therefore, in one embodiment, an antagonist of HNANL may be administered to a subject to treat or prevent a cancer. Such a cancer may include, but is not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HNANL may be used directly as an antagonist or indirectly as a targeting or delivery mechanism for bringing a pharmaceutical agent to cells or tissue which express HNANL.

In an additional embodiment, a vector expressing the complement of the polynucleotide encoding HNANL may be administered to a subject to treat or prevent a cancer including, but not limited to, those described above.

In another embodiment, an antagonist of HNANL may be administered to a subject to treat or prevent an autoimmune disorder. Such a disorder may include, but is not limited to, AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. In one aspect, an antibody which specifically binds HNANL may be used directly as an antagonist or indirectly as a targeting or delivery mechanism for bringing a pharmaceutical agent to cells or tissue which express HNANL.

In an additional embodiment, a vector expressing the complement of the polynucleotide encoding HNANL may be administered to a subject to treat or prevent an autoimmune disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HNANL may be produced using methods which are generally known in the art. In particular, purified HNANL may be used to produce antibodies or to screen libraries of pharmaceutical agents to identify those which specifically bind HNANL. Antibodies to HNANL may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HNANL or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HNANL have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HNANL amino acids may be fused with those of another protein, such as KLH, and antibodies to the chimeric molecule may be produced.

Monoclonal antibodies to HNANL may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HNANL-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for HNANL may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HNANL and its specific antibody. A two-site, monoclonal-based immunoassay utilizing monoclonal antibodies reactive to two non-interfering HNANL epitopes is preferred, but a competitive binding assay may also be employed (Maddox, supra).

In another embodiment of the invention, the polynucleotides encoding HNANL, or any fragment or complement thereof, may be used for therapeutic purposes. In one aspect, the complement of the polynucleotide encoding HNANL may be used in situations in which it would be desirable to block the transcription of the mRNA. In particular, cells may be transformed with sequences complementary to polynucleotides encoding HNANL. Thus, complementary molecules or fragments may be used to modulate HNANL activity, or to achieve regulation of gene function. Such technology is now well known in the art, and sense or antisense oligonucleotides or larger fragments can be designed from various locations along the coding or control regions of sequences encoding HNANL.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequences complementary to the polynucleotides of the gene encoding HNANL. (See, e.g., Sambrook, supra; and Ausubel, supra.)

Genes encoding HNANL can be turned off by transforming a cell or tissue with expression vectors which express high levels of a polynucleotide, or fragment thereof, encoding HNANL. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HNANL. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches,* Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HNANL.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HNANL. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HNANL, antibodies to HNANL, and mimetics, agonists, antagonists, or inhibitors of HNANL. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HNANL, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HNANL or fragments thereof, antibodies of HNANL, and agonists, antagonists or inhibitors of HNANL, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio of therapeutic to toxic effects is the therapeutic index, and it can be expressed as the ED50/LD50 ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 µg to 100,000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HNANL may be used for the diagnosis of disorders characterized by expression of HNANL, or in assays to monitor patients being treated with HNANL or agonists, antagonists, or inhibitors of HNANL. Antibodies useful for diagnostic purposes may be prepared in the same manner as described above for therapeutics. Diagnostic assays for HNANL include methods which utilize the antibody and a label to detect HNANL in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HNANL, including ELISAs, RIAs, and FACS, are known in the art and provide a basis for diagnosing altered or abnormal levels of HNANL expression. Normal or standard values for HNANL expression are established by combining body fluids or cell extracts taken from normal mammalian subjects, preferably human, with antibody to HNANL under conditions suitable for complex formation. The amount of standard complex formation may be quantitated by various methods, preferably by photometric means. Quantities of HNANL expressed in subject, control, and disease samples from biopsied tissues are compared with the standard values. Deviation between standard and subject values establishes the parameters for diagnosing disease.

In another embodiment of the invention, the polynucleotides encoding HNANL may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HNANL may be correlated with disease. The diagnostic assay may be used to determine absence, presence, and excess expression of HNANL, and to monitor regulation of HNANL levels during therapeutic intervention.

In one aspect, hybridization with PCR probes which are capable of detecting polynucleotide sequences, including genomic sequences, encoding HNANL or closely related molecules may be used to identify nucleic acid sequences which encode HNANL. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HNANL, alleles, or related sequences.

Probes may also be used for the detection of related sequences, and should preferably contain at least 50% of the nucleotides from any of the HNANL encoding sequences. The hybridization probes of the subject invention may be DNA or RNA and may be derived from the sequence of SEQ ID NO:2 or from genomic sequences including promoters, enhancers, and introns of the HNANL gene.

Means for producing specific hybridization probes for DNAs encoding HNANL include the cloning of polynucleotide sequences encoding HNANL or HNANL derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding HNANL may be used for the diagnosis of a disorder associated with expression of HNANL. Examples of such a disorder include, but are not limited to, cancer, such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and autoimmune disorders, such as AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjbgren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. The polynucleotide sequences encoding HNANL may be used in Southern or northern analysis, dot blot, or other membrane-based technologies; in PCR technologies; in dipstick, pin, and ELISA assays; and in microarrays utilizing fluids or tissues from patients to detect altered HNANL expression. Such qualitative or quantitative methods are well known in the art.

In a particular aspect, the nucleotide sequences encoding HNANL may be useful in assays that detect the presence of associated disorders, particularly those mentioned above. The nucleotide sequences encoding HNANL may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HNANL in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HNANL, a normal or standard profile for expression is established. This may be accomplished by combining body fluids or cell extracts taken from normal subjects, either animal or human, with a sequence, or a fragment thereof, encoding HNANL, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HNANL may involve the use of PCR. These oligomers may be chemically synthesized, generated enzymatically, or produced in vitro. Oligomers will preferably contain a fragment of a polynucleotide encoding HNANL, or a fragment of a polynucleotide complementary to the polynucleotide encoding HNANL, and will be employed under optimized conditions for identification of a specific gene or condition. Oligomers may also be employed under less stringent conditions for detection or quantitation of closely related DNA or RNA sequences.

Methods which may also be used to quantitate the expression of HNANL include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding HNANL may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding HNANL on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., AT to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, HNANL, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HNANL and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with HNANL, or fragments thereof, and washed. Bound HNANL is then detected by methods well known in the art. Purified HNANL can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HNANL specifically compete with a test compound for binding HNANL. In this manner, antibodies can be used to detect the presence of any peptide which shares one or more antigenic determinants with HNANL.

In additional embodiments, the nucleotide sequences which encode HNANL may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. BRSTNOT07 cDNA Library Construction

The breast tissue cDNA library was constructed using non-tumorous breast tissue isolated from a 43-year old Caucasian female during unilateral extended simple mastectomy. Pathology indicated mildly proliferative fibrocystic changes with epithelial hyperplasia, papillomatosis, and duct ectasia. Pathology for the associated tumor tissue indicated invasive grade 4, nuclear grade 3 mammary adenocarcinoma with extensive necrosis. Approximately 50 percent of the tumor was intraductal (comedo carcinoma). A microscopic focus of residual intraductal carcinoma was identified at the biopsy site in the lower inner quadrant of the right breast. The overlying skin, nipple, deep fascia, and axillary lymph nodes were negative for tumor. The frozen tissue was homogenized and lysed in TRIZOL reagent (1 gm tissue/10 ml TRIZOL; life Technologies Homogenizer Polytron PT-3000 (Brinkmann Instruments, Westbury, N.Y.). After a brief incubation on ice, chloroform was added (1:5 v/v) and the lysate was centrifuged. The upper chloroform layer was removed to a fresh tube and the RNA extracted with isopropanol, resuspended in DEPC-treated water, and DNase treated for 25 min at 37° C. The RNA was re-extracted twice with acid phenol-chloroform pH 4.7 and precipitated using 0.3M sodium acetate and 2.5 volumes ethanol. The mRNA was then isolated using the OLIGOTEX, CA), and cDNA synthesis was initiated using a NotI-oligo(dT) primer. cDNA was blunted, ligated to EcoRI adaptors, digested with NotI, and ligated into the pINCY vector (Pharmaceuticals, Palo Alto).

II. Isolation and Sequencing of cDNA Clones

Plasmid DNA was released from the cells and purified using the REAL Prep 96 Plasmid Kit (Catalog #26173; QIAGEN). The recommended protocol was employed except for the following changes: 1) the bacteria were cultured in 1 ml of sterile Terrific Broth (Catalog #22711, Life Technologies) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94: 441f), using a Hamilton Micro Lab 2200 (Hamilton) in combination with Peltier Thermal Cyclers (MJ Research) and Applied Biosystems 377 DNA Sequencing Systems.

III. Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (See, e.g., Altschul, S. F. (1993) J. Mol. Evol 36:290–300; and Altschul et al. (1990) J. Mol. Biol. 215:403410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

Additionally, sequences identified from cDNA libraries may be analyzed to identify those gene sequences encoding conserved protein motifs using an appropriate analysis program, e.g., the Block 2 Bioanalysis Program (Incyte Pharmaceuticals). This motif analysis program, based on sequence information contained in the Swiss-Prot Database and PROSITE, is a method of determining the function of uncharacterized proteins translated from genomic or cDNA sequences. (See, e.g., Bairoch, A. et al. (1997) Nucleic Acids Res. 25:217–221; and Attwood, T. K. et al. (1997) J. Chem. Inf. Comput. Sci. 37:417–424.) PROSITE may be used to identify common functional or structural domains in divergent proteins. The method is based on weight matrices. Motifs identified by this method are then calibrated against the SWISS-PROT database in order to obtain a measure of the chance distribution of the matches.

In another alternative, Hidden Markov models (HMMs) may be used to find protein domains, each defined by a dataset of proteins known to have a common biological function. (See, e.g., Pearson, W. R. and D. J. Lipman (1988) Proc. Natl. Acad. Sci. 85:2444–2448; and Smith, T. F. and M. S. Waterman (1981) J. Mol. Biol. 147:195–197.) HMMs were initially developed to examine speech recognition patterns, but are now being used in a biological context to analyze protein and nucleic acid sequences as well as to model protein structure. (See, e.g., Krogh, A. et al. (1994) J. Mol. Biol. 235:1501–1531; and Collin, M. et al. (1993) Protein Sci. 2:305–314.) HMMs have a formal probabilistic basis and use position-specific scores for amino acids or nucleotides. The algorithm continues to incorporate information from newly identified sequences to increase its motif analysis capabilities.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST are used to search for identical or related molecules in nucleotide databases such as GenBank or LIFESEQ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

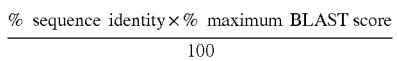

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding HNANL occurs. Abundance and percent abundance are also reported. Abundance directly reflects the number of times a particular transcript is represented in a cDNA library, and percent abundance is abundance divided by the total number of sequences examined in the cDNA library.

V. Extension of HNANL Encoding Polynucleotides

The nucleic acid sequence of Incyte Clone 2125668 was used to design oligonucleotide primers for extending a partial nucleotide sequence to full length. One primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (Life Technologies) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier Thermal Cycler (MJ Research), beginning with 40 pmol of each primer and the recommended concentrations of all other components of the kit, with the following parameters:

| Step 1  | 94° C. for 1 min (initial denaturation)            |
| ------- | -------------------------------------------------- |
| Step 2  | 65° C. for 1 min                                   |
| Step 3  | 68° C. for 6 min                                   |
| Step 4  | 94° C. for 15 sec                                  |
| Step 5  | 65° C. for 1 min                                   |
| Step 6  | 68° C. for 7 min                                   |
| Step 7  | Repeat steps 4 through 6 for an additional 15 cycles |
| Step 8  | 94° C. for 15 sec                                  |
| Step 9  | 65° C. for 1 min                                   |
| Step 10 | 68° C. for 7:15 min                                |
| Step 11 | Repeat steps 8 through 10 for an additional 12 cycles |
| Step 12 | 72° C. for 8 min                                   |
| Step 13 | 40° C. (and holding)                               |

A 5 μl to 10 μl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK (QIAGEN Inc.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2 to 3 hours, or overnight at 16° C. Competent E. coli cells (in 40 μl of appropriate media) were transformed with 3 μl of ligation mixture and cultured in 80 μl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1.) containing carbenicillin (2× carb). The following day, several colonies were randomly picked from each plate and cultured in 150 μl of liquid LB/2× Carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec                                  |
| ------ | -------------------------------------------------- |
| Step 2 | 94° C. for 20 sec                                  |
| Step 3 | 55° C. for 30 sec                                  |
| Step 4 | 72° C. for 90 sec                                  |
| Step 5 | Repeat steps 2 through 4 for an additional 29 cycles |
| Step 6 | 72° C. for 180 sec                                 |
| Step 7 | 4° C. (and holding)                                |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 (National Biosciences) and labeled by combining 50 pmol of each oligomer, 250 μCi of [γ-$^{32}$P] adenosine triphosphate (Amersham Pharmacia), and T4 polynucleotide kinase (DuPont NEN, Boston, Mass.). The labeled oligonucleotides are substantially purified using a SEPHADEX G-25 superfine resin column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba1, or Pvu II (DuPont NEN, Boston, Mass.).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Eastman Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the HNANL-encoding sequences, or any parts thereof, are used to detect, decrease, or inhibit expression of naturally occurring HNANL. Although use of oligonucleotides comprising from about 15 to 30 base pairs is described, essentially the same procedure is used with smaller or with larger sequence fragments. Appropriate oligonucleotides are designed using Oligo 4.06 software (National Biosciences) and the coding sequence of HNANL. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HNANL-encoding transcript.

IX. Expression of HNANL

Expression of HNANL is accomplished by subcloning the cDNA into an appropriate vector and transforming the vector into host cells. This vector contains an appropriate promoter, e.g., β-galactosidase, upstream of the cloning site, operably associated with the cDNA of interest. (See, e.g., Sambrook, supra, pp. 404–433; and Rosenberg, M. et al. (1983) Methods Enzymol. 101:123–138.)

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of HNANL into bacterial growth media which can be used directly in the following assay for activity.

X. Demonstration of HNANL Activity

The activity of the enzyme HNANL in a sample can be determined by measuring the conversion of the substrate, N-acetylneuraminic acid, into pyruvate and N-acetyl-D-mannosamine, and the subsequent reduction of pyruvate to lactate by lactate dehydrogenase and the reducing agent diphosphopyridine nucleotide (DPNH). The change in oxidation state of DPNH produces a change in optical density, which can be measured spectrophotometrically. Varying amounts of HNANL are incubated with a fixed amount of N-acetylneuraminic acid in a cuvette containing 0.1 M potassium phosphate buffer, pH 7.2, containing excess lactate dehydrogenase and DHNP. The reaction is allowed to proceed to completion, and the change in optical density is measured. This change is proportional to the activity of HNANL in the sample. (Meysick, K. C. et al. supra).

XI. Production of HNANL Specific Antibodies

HNANL substantially purified using PAGE electrophoresis (see, e.g., Harrington, M. G. (1990) Methods Enzymol. 182:488–495), or other purification techniques, is used to immunize rabbits and to produce antibodies using standard protocols.

Alternatively, the HNANL amino acid sequence is analyzed using LASERGENE software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems Peptide Synthesizer Model 431 A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring HNANL Using Specific Antibodies

Naturally occurring or recombinant HNANL is substantially purified by immunoaffinity chromatography using antibodies specific for HNANL. An immunoaffinity column is constructed by covalently coupling anti-HNANL antibody to an activated chromatographic resin, such as CNBr-activated SEPHAROSE (Amersham Pharmacia Biotech). After the coupling, the resin is blocked and washed according to the manufacturer's instructions.

Media containing HNANL are passed over the immunoaffinity column, and the column is washed under conditions that allow the preferential absorbance of HNANL (e.g., high ionic strength buffers in the presence of detergent). The column is eluted under conditions that disrupt antibody/HNANL binding (e.g., a buffer of pH 2 to pH 3, or a high concentration of a chaotrope, such as urea or thiocyanate ion), and HNANL is collected.

XIII. Identification of Molecules Which Interact with HNANL

HNANL, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled HNANL, washed, and any wells with labeled HNANL complex are assayed. Data obtained using different concentrations of HNANL are used to calculate values for the number, affinity, and association of HNANL with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A substantially purified polypeptide comprising the amino acid sequence of SEQ ID NO: 1 or a fragment of SEQ ID NO: 1 having N-acetylneuraminate lyase activity.

2. A pharmaceutical composition comprising the polypeptide of claim 1 in conjunction with a suitable pharmaceutical carrier.

* * * * *

```
                          SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
         (A) LENGTH: 320 amino acids
         (B) TYPE: amino acid
         (C) STRANDEDNESS: single
         (D) TOPOLOGY: linear (vii) IMMEDIATE SOURCE:
         (A) LIBRARY: BRSTNOT07
         (B) CLONE: 2125668

(xi) SEQUENCE DESCRIPTION: SEQ ID NO:1:

Met Ala Phe Pro Lys Lys Lys Leu Gln Gly Leu Val Ala Ala Thr Ile
1               5                  10                  15

Thr Pro Met Thr Glu Asn Gly Glu Ile Asn Phe Ser Val Ile Gly Gln
            20                  25                  30

Tyr Val Asp Tyr Leu Val Lys Glu Gln Gly Val Lys Asn Ile Phe Val
        35                  40                  45

Asn Gly Thr Thr Gly Glu Gly Leu Ser Leu Ser Val Ser Glu Arg Arg
    50                  55                  60

Gln Val Ala Glu Glu Trp Val Thr Lys Gly Lys Asp Lys Leu Asp Gln
65                  70                  75                  80

Val Ile Ile His Val Gly Ala Leu Ser Leu Lys Glu Ser Gln Glu Leu
                85                  90                  95

Ala Gln His Ala Ala Glu Ile Gly Ala Asp Gly Ile Ala Val Ile Ala
            100                 105                 110

Pro Phe Phe Leu Lys Pro Trp Thr Lys Asp Ile Leu Ile Asn Phe Leu
        115                 120                 125

Lys Glu Val Ala Ala Ala Pro Ala Leu Pro Phe Tyr Tyr Tyr His
    130                 135                 140

Ile Pro Ala Leu Thr Gly Val Lys Ile Arg Ala Glu Glu Leu Leu Asp
145                 150                 155                 160

Gly Ile Leu Asp Lys Ile Pro Thr Phe Gln Gly Leu Lys Phe Ser Asp
                165                 170                 175

Thr Asp Leu Leu Asp Phe Gly Gln Cys Val Asp Gln Asn Arg Gln Gln
            180                 185                 190

Gln Phe Ala Phe Leu Phe Gly Val Asp Glu Gln Leu Leu Ser Ala Leu
        195                 200                 205

Val Met Gly Ala Thr Gly Ala Val Gly Ser Thr Tyr Asn Tyr Leu Gly
    210                 215                 220

Lys Lys Thr Asn Gln Met Leu Glu Ala Phe Glu Gln Lys Asp Phe Ser
225                 230                 235                 240

Leu Ala Leu Asn Tyr Gln Phe Cys Ile Gln Arg Phe Ile Asn Phe Val
```

```
                    245                 250                 255
Val Lys Leu Gly Phe Gly Val Ser Gln Thr Lys Ala Ile Met Thr Leu
                260                 265                 270

Val Ser Gly Ile Pro Met Gly Pro Pro Arg Leu Pro Leu Gln Lys Ala
                275                 280                 285

Ser Arg Glu Phe Thr Asp Ser Ala Glu Ala Lys Leu Lys Ser Leu Asp
        290                 295                 300

Phe Leu Ser Phe Thr Asp Leu Lys Asp Gly Asn Leu Glu Ala Gly Ser
305                 310                 315                 320

(2) INFORMATION FOR SEQ ID NO:2:

(i) SEQUENCE CHARACTERISTICS:
        (A) LENGTH: 2536 base pairs
        (B) TYPE: nucleic acid
        (C) STRANDEDNESS: single
        (D) TOPOLOGY: linear (vii) IMMEDIATE SOURCE:
        (A) LIBRARY: BRSTNOT07
        (B) CLONE: 2125668

(xi) SEQUENCE DESCRIPTION: SEQ ID NO:2:

CAAGAGCGGA GGCCTGGAAG GGGAAACTGA AGCAGAAAGA GGTTACTTAA TGGGCTCAAG      60

GTCACCTACC TGACCTACCA GCAGCTCAAT GGCCTTCCCA AGAAGAAAC TTCAGGGTCT     120

TGTGGCTGCA ACCATCACGC CAATGACTGA GAATGGAGAA ATCAACTTTT CAGTAATTGG    180

TCAGTATGTG GATTATCTTG TGAAAGAACA GGGAGTGAAG AACATTTTTG TGAATGGCAC    240

AACAGGAGAA GGCCTGTCCC TGAGCGTCTC AGAGCGTCGC CAGGTTGCAG AGGAGTGGGT    300

GACAAAAGGG AAGGACAAGC TGGATCAGGT GATAATTCAC GTAGGAGCAC TGAGCTTGAA    360

GGAGTCACAG GAACTGGCCC AACATGCAGC AGAAATAGGA GCTGATGGCA TCGCTGTCAT    420

TGCACCGTTC TTCCTCAAGC CATGGACCAA AGATATCCTG ATTAATTTCC TAAAGGAAGT    480

GGCTGCTGCC GCCCCTGCCC TGCCATTTTA TTACTATCAC ATTCCTGCCT TGACAGGGGT    540

AAAGATTCGT GCTGAGGAGT TGTTGGATGG GATTCTGGAT AAGATCCCCA CCTTCCAAGG    600

GCTGAAATTC AGTGATACAG ATCTCTTAGA CTTCGGGCAA TGTGTTGATC AGAATCGCCA    660

GCAACAGTTT GCTTTCCTTT TTGGGGTGGA TGAGCAATTG TTGAGTGCTC TGGTGATGGG    720

AGCAACTGGA GCAGTGGGCA GTACCTATAA CTACCTGGGA AAAAAGACAA ACCAGATGTT    780

GGAGGCTTTT GAACAAAAGG ACTTCTCTTT AGCCCTGAAC TATCAGTTTT GTATCCAGAG    840

ATTTATCAAC TTTGTTGTCA AACTAGGTTT TGGAGTGTCA CAGACCAAAG CCATCATGAC    900

TCTGGTCTCT GGGATTCCAA TGGGCCCACC CCGGCTTCCA CTGCAGAAAG CCTCCAGGGA    960

GTTTACTGAT AGTGCTGAAG CTAAACTGAA GAGCCTGGAT TTCCTTTCTT TCACTGATTT   1020

AAAGGATGGA AACTTGGAAG CTGGTAGCTA GTGCCTCTCT ATCAAATCAG GGTTTGCACC   1080

TTGAGACATA ATCTACCTTA AATAGTGCAT TTTTTTCTCA GGGAATTTTA GATGAACTTG   1140

AATAAACTCT CCTAGCAAAT GAAATCTCAC AATAAGCATT GAGGTACCTT TTGTGAGCCT   1200

TAAAAGTCT TATTTTGTGA AGGGCAAAA ACTCTAGGAG TCACAACTCT CAGTCATTCA    1260

TTTCACAGAT TTTTTTGTGG AGAAATTTCT GTTTATATGG ATGAAATGGA ATCAAGAGGA   1320

AAATTGTAAT TGATTAATTC CATCTGTCTT TAGGAGCTCT CATTATCTCG GTCTCTGGTT   1380

CCTAATCCTA TTTTAAAGTT GTCTAATTTT AAACCACTAT AATATGTCTT CATTTAATA    1440

AATATTCATT TGGAATCTAG GAAAACTCTG AGCTACTGCA TTTAGGCAGG CACTTTAATA   1500
```

-continued

```
CCAAACTGTA ACATGTCTCA ACTGTATACA ACTCAAAATA CACCAGCTCA TTTGGCTGCT    1560

CAGTCTAACT CTAGAATGGA TGCTTTTGAA TTCATTTCGA TGTCACCACT TTTCGCTCTT    1620

TAAAAACACT GGGTCAGGTG AGGACTTGTT TCAGTTCCTA TAACTAAGTA AAGGGCGGCT    1680

TTCTCATAAC AAAGGAAAAA GTCTTCCCCA AGATGAATT TAAGTCTCCA CTTTTTTCTA     1740

TACAGAAAAC TCAAAACTCA AAGTTTCAAA GAACCAAAGG ACTCTTCCTC TGGGCACCAC    1800

AAACTTCCCC TTCCTCCACT GAGAAGACTG TCTCTCCCGC AGGACCCTGA ATTATTGAAA    1860

TCGAAGGCTG ACTTCCTTTC TGCAGTGAGC CCAGGGGCTA ATGTTATTAT CCTGTCACAC    1920

TTGCAACTAG TGACTTTTGT TTAGTGATAG AAGATTTGGG GAGGACCCAA AGGACTCAGA    1980

ACTTTCTCTC CATACCTCCT TTTACTCTTT TCTTTCTGTG TAATGTATCA ACAACTGTTT    2040

AATCTCCCTT CTAACAAACC TTGATATAAG CTTTCTGATA TCAAAGTATA TTGACAGTTA    2100

ACCCTTACTG ATTTTAAACT TGACTATCCA GTCTGTTAAT TACCTAAGAT TTTGTTTTCA    2160

TTTCATCTCT AATTGTTTTG ATCATTGGCA GAGAAAGAGT ATTTGAAATT CATATCAGTT    2220

TTGCTCCTTA TTTTAATCTC TTTGAATTAA AAATAAAACT TTTTCAAAAT GGAAATTTGA    2280

AATTATAAGT AGACTTCAAT TATCTTTGCT AATCCTCTCT TTAATTAGTC AGCTAGTTAA    2340

AAGTTGTTAT ATTCATATAT CCTCAACCCT CTTTTTGCCT TTGTAGCTTT TAATTTCCTG    2400

AAAGAAGAAA ATGAGTTGTT CGTTTTTGGT TCTGAGGATG TGATATCCGT ACTTACTGAT    2460

ACTAAAGCCA AATTTAAATT CTAAAATTAA TTCTTGGGTA TCCAATAAAC AAAGAACTAT    2520

TTTTCAAAAA AAAAAA                                                    2536
```

(2) INFORMATION FOR SEQ ID NO:3:

(i) SEQUENCE CHARACTERISTICS:
        (A) LENGTH: 297 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: GI 42131

(xi) SEQUENCE DESCRIPTION: SEQ ID NO:3:

```
Met Ala Thr Asn Leu Arg Gly Val Met Ala Ala Leu Leu Thr Pro Phe
 1               5                  10                  15

Asp Gln Gln Gln Ala Leu Asp Lys Ala Ser Leu Arg Arg Leu Val Gln
                20                  25                  30

Phe Asn Ile Gln Gln Gly Ile Asp Gly Leu Tyr Val Gly Gly Ser Thr
            35                  40                  45

Gly Glu Ala Phe Val Gln Ser Leu Ser Glu Arg Glu Gln Val Leu Glu
        50                  55                  60

Ile Val Ala Glu Glu Gly Lys Gly Lys Ile Lys Leu Ile Ala His Val
65                  70                  75                  80

Gly Cys Val Thr Thr Ala Glu Ser Gln Gln Leu Ala Ala Ser Ala Lys
                85                  90                  95

Arg Tyr Gly Phe Asp Ala Val Ser Ala Val Thr Pro Phe Tyr Tyr Pro
                100                 105                 110

Phe Ser Phe Glu Glu His Cys Asp His Tyr Arg Ala Ile Ile Asp Ser
            115                 120                 125

Ala Asp Gly Leu Pro Met Val Val Tyr Asn Ile Pro Ala Leu Ser Gly
        130                 135                 140

Val Lys Leu Thr Leu Asp Gln Ile Asn Thr Leu Val Thr Leu Pro Gly
```

```
                         145                 150                 155                 160
    Val Gly Ala Leu Lys Gln Thr Ser Gly Asp Leu Tyr Gln Met Glu Gln
                     165                 170                 175

Ile Arg Arg Glu His Pro Asp Leu Val Leu Tyr Asn Gly Tyr Asp Glu
                 180                 185                 190

Ile Phe Ala Ser Gly Leu Leu Ala Gly Ala Asp Gly Ile Gly Ser
                 195                 200                 205

Thr Tyr Asn Ile Met Gly Trp Arg Tyr Gln Gly Ile Val Lys Ala Leu
                 210                 215                 220

Lys Glu Gly Asp Ile Gln Thr Ala Gln Lys Leu Gln Thr Glu Cys Asn
    225                 230                 235                 240

Lys Val Ile Asp Leu Leu Ile Lys Thr Gly Val Phe Arg Gly Leu Lys
                     245                 250                 255

Thr Val Leu His Tyr Met Asp Val Val Ser Val Pro Leu Cys Arg Lys
                     260                 265                 270

Pro Phe Gly Pro Val Asp Glu Lys Tyr Gln Pro Glu Leu Lys Ala Leu
                 275                 280                 285

Ala Gln Gln Leu Met Gln Glu Arg Gly
    290                 295

(2) INFORMATION FOR SEQ ID NO:4:

(i) SEQUENCE CHARACTERISTICS:
        (A) LENGTH: 318 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: GI 1016806

(xi) SEQUENCE DESCRIPTION: SEQ ID NO:4:

Met Phe Val Phe Leu Ala Ile Ser Met Ala Lys Ser Ala Ala Ala Glu
    1               5                   10                  15

Ala Thr Thr Gly Pro Lys Gly Lys Ser Ala Lys Ser Leu Lys Gly Leu
                    20                  25                  30

Phe Ser Ala Leu Leu Val Ser Phe Asn Glu Asp Gly Thr Ile Asn Glu
                35                  40                  45

Lys Gly Leu Arg Glu Ile Val Arg Tyr Asn Ile Asp Lys Met Lys Ile
        50                  55                  60

Asp Gly Leu Tyr Val Gly Gly Ser Thr Gly Glu Asn Phe Glu Leu Ser
    65                  70                  75                  80

Thr Glu Glu Lys Lys Gln Ile Phe Arg Ile Ala Lys Asp Glu Ala Lys
                    85                  90                  95

Asp Gln Val Ala Leu Ile Ala Gln Val Gly Ser Ile Asn Ile His Glu
                100                 105                 110

Ser Ile Glu Leu Gly Lys Tyr Ala Thr Glu Leu Gly Tyr Asn Cys Leu
                115                 120                 125

Ser Ala Val Thr Pro Phe Tyr Tyr Lys Phe Thr Phe Pro Glu Ile Lys
            130                 135                 140

Asn Tyr Tyr Asn Thr Ile Val Asn Ala Thr Gly Met Asn Met Ile Val
    145                 150                 155                 160

Tyr Ser Ile Pro Ala Leu Thr Gly Val Ser Met Thr Ala Asp Gln Phe
                    165                 170                 175

Gly Glu Leu Phe Glu Asn Pro Lys Ile Ile Gly Val Lys Phe Thr Ala
                180                 185                 190
```

-continued

```
Gly Asp Phe Tyr Leu Leu Glu Arg Val Lys Arg Ala Tyr Pro Asp His
        195                 200                 205
Leu Ile Trp Ala Gly Phe Asp Glu Met Met Leu Pro Ala Cys Ser Leu
    210                 215                 220
Gly Ile Asp Gly Ala Ile Gly Ser Thr Phe Asn Val Asn Ala Lys Arg
225                 230                 235                 240
Ala Arg Gln Ile Phe Glu Leu Ser Lys Ala Gly Lys Tyr Asp Glu Ala
            245                 250                 255
Leu Glu Val Gln His Val Thr Asn Asp Leu Ile Ala Gly Ile Leu Ser
            260                 265                 270
Asn Gly Leu Tyr Leu Thr Ile Lys Glu Leu Met Arg Leu Asp Gly Val
        275                 280                 285
Asp Ala Gly Tyr Cys Arg Glu Pro Met Thr Lys Ala Leu Thr Pro Ala
        290                 295                 300
Gln Val Ala Phe Ala Lys Gln Leu Lys Glu Lys Tyr Leu Leu
305                 310                 315
```